United States Patent
Errico et al.

(10) Patent No.: US 9,987,151 B2
(45) Date of Patent: Jun. 5, 2018

(54) MECHANISM FOR EFFICIENT DONNING AND DOFFING OF AN EXOSKELETON

(71) Applicant: THE REGENTS OF THE UNIVERSITY OF CALIFORNIA, Oakland, CA (US)

(72) Inventors: Nicholas Errico, Berkeley, CA (US); Homayoon Kazerooni, Berkeley, CA (US); Yoon Jung Jeong, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days. days.

(21) Appl. No.: 15/190,920

(22) Filed: Jun. 23, 2016

(65) Prior Publication Data

US 2016/0374836 A1 Dec. 29, 2016

Related U.S. Application Data

(60) Provisional application No. 62/183,407, filed on Jun. 23, 2015.

(51) Int. Cl.
*A61F 5/01* (2006.01)
*A61F 2/76* (2006.01)
(Continued)

(52) U.S. Cl.
CPC ............... *A61F 2/76* (2013.01); *A61F 2/605* (2013.01); *A61F 2/64* (2013.01); *A61H 1/0255* (2013.01);
(Continued)

(58) Field of Classification Search
CPC ............. Y10T 24/2143; Y10T 24/2147; Y10T 24/2142; Y10T 24/216; Y10T 24/2183;
(Continued)

(56) References Cited

U.S. PATENT DOCUMENTS

| 314,550 A | * | 3/1885 | Vetsburg | A43C 11/1406 24/1 SK |
| 897,115 A | * | 8/1908 | Lindberg et al. | A44B 11/04 24/71 ST |

(Continued)

OTHER PUBLICATIONS

International Search Report and Written Opinion issued in the corresponding application PCT/US16/38999 dated Sep. 14, 2016.

*Primary Examiner* — Jason W San
(74) *Attorney, Agent, or Firm* — Kwan & Olynick LLP (57) ABSTRACT

A manual apparatus of the present invention enables quick connection and disconnection of an exoskeleton leg from a remaining body of an exoskeleton. The apparatus comprises a cavity defined by a housing coupled to the remaining body of the exoskeleton; a latch coupled to the remaining body of the exoskeleton, the latch comprising a latching feature; a clip body including a projection element extending from an end thereof, the clip body coupled to the exoskeleton leg; a handle rotatably coupled to a clip base on the clip body; and a hook rotatably coupled to the handle. When the hook is engaged with the latching feature and the handle rotated from a first unlatched position to a second latched position, the projection element moves inside the cavity.

23 Claims, 11 Drawing Sheets

(51) Int. Cl.
*A61F 2/60* (2006.01)
*A61F 2/64* (2006.01)
*A61H 3/00* (2006.01)
*A61H 1/02* (2006.01)

(52) U.S. Cl.
CPC ........ *A61H 3/00* (2013.01); *A61H 2201/1207* (2013.01); *A61H 2201/1454* (2013.01); *A61H 2201/1463* (2013.01); *A61H 2201/164* (2013.01); *A61H 2201/165* (2013.01); *A61H 2201/1628* (2013.01); *A61H 2201/1676* (2013.01); *A61H 2201/5007* (2013.01)

(58) Field of Classification Search
CPC ... A43C 11/1406; A44B 11/125; A44B 11/12; A61F 5/0123
USPC ................ 128/882; 602/16, 23–28; 24/592.1
See application file for complete search history.

(56) References Cited

U.S. PATENT DOCUMENTS

| | | | | |
|---|---|---|---|---|
| 1,097,296 | A * | 5/1914 | Button | A43C 11/1406 24/69 SK |
| 1,220,435 | A * | 3/1917 | Lauer | F16G 11/12 24/68 R |
| 1,393,721 | A * | 10/1921 | Otten | A44B 11/12 24/191 |
| 1,395,713 | A * | 11/1921 | Humphrey | A44B 11/12 24/191 |
| 1,396,020 | A * | 11/1921 | Buchsbaum | A44B 11/12 24/191 |
| 1,493,888 | A * | 5/1924 | Miller | A44B 11/12 24/191 |
| 3,317,967 | A * | 5/1967 | Rounds | A44B 11/12 24/272 |
| 3,696,471 | A * | 10/1972 | Mermelstein | A44B 11/12 24/193 |
| 4,051,611 | A * | 10/1977 | Chalmers | A43C 11/1413 24/68 SK |
| 4,207,776 | A * | 6/1980 | Helt | F16G 5/16 24/31 B |
| 4,424,636 | A * | 1/1984 | Everest | A43C 11/1406 24/68 SK |
| 4,594,752 | A * | 6/1986 | Garner, Sr. | F16G 11/101 24/132 R |
| 4,651,392 | A * | 3/1987 | Olivieri | A43C 11/142 24/68 SK |
| 4,670,946 | A * | 6/1987 | Olivieri | A43C 11/1413 24/68 A |
| 5,172,454 | A * | 12/1992 | Martignago | A43C 11/1406 24/68 SK |
| 5,271,649 | A | 12/1993 | Gromotka | |
| 5,383,258 | A * | 1/1995 | Nicoletti | A43C 11/1406 24/68 SK |
| 5,530,997 | A * | 7/1996 | Tessari | A43C 11/146 24/593.11 |
| 5,575,045 | A * | 11/1996 | Chu | A43C 11/146 24/68 SK |
| 5,592,722 | A * | 1/1997 | Foscaro | A43C 11/00 24/68 SK |
| 5,630,253 | A * | 5/1997 | Benoit | A43C 11/1406 24/70 SK |
| 5,715,582 | A * | 2/1998 | Zorzi | A43C 11/1406 24/71 SK |
| 5,845,371 | A * | 12/1998 | Chen | A43C 11/1406 24/68 SK |
| 5,884,370 | A * | 3/1999 | Bergamin | A43C 11/1406 24/68 SK |
| D413,197 | S * | 8/1999 | Faye | D2/978 |
| 6,185,797 | B1 * | 2/2001 | Lan | A44B 11/12 24/647 |
| 6,299,588 | B1 | 10/2001 | Fratrick | |
| 7,190,141 | B1 | 3/2007 | Ashratiuon et al. | |
| 7,798,983 | B2 | 9/2010 | Katoh et al. | |
| 7,967,765 | B2 * | 6/2011 | Nathanson | A61F 5/0123 602/16 |
| 8,409,298 | B2 | 4/2013 | Perkins et al. | |
| 8,652,075 | B2 * | 2/2014 | Takahashi | A61H 1/0244 601/34 |
| 8,875,354 | B2 * | 11/2014 | Miessmer | F16L 33/025 24/19 |
| 9,101,451 | B2 | 8/2015 | Chugunov | |
| 9,339,083 | B2 * | 5/2016 | Benetti | A43C 11/142 |
| 2002/0088386 | A1 * | 7/2002 | Veh | A44B 11/125 114/39.18 |
| 2002/0173739 | A1 * | 11/2002 | Jensen | A43B 7/1495 602/27 |
| 2003/0014001 | A1 * | 1/2003 | Martin | A61F 5/0127 602/27 |
| 2003/0100854 | A1 * | 5/2003 | Rossi | A61F 5/0193 602/16 |
| 2005/0075594 | A1 * | 4/2005 | Hepburn | A61F 5/0125 602/16 |
| 2005/0159691 | A1 * | 7/2005 | Turrini | A61F 5/0123 602/16 |
| 2005/0192523 | A1 * | 9/2005 | Knecht | A61F 5/0123 602/26 |
| 2006/0264790 | A1 * | 11/2006 | Kruijsen | A61F 5/0193 602/16 |
| 2009/0178256 | A1 * | 7/2009 | Toth | A44B 11/125 24/71 ST |
| 2009/0287127 | A1 * | 11/2009 | Hu | A61F 5/0111 602/27 |
| 2010/0331750 | A1 * | 12/2010 | Ingimundarson | A61F 5/0123 602/26 |
| 2011/0041301 | A1 * | 2/2011 | Liang | A44B 11/125 24/68 CD |
| 2012/0289878 | A1 * | 11/2012 | Schwenn | A61F 5/0193 602/23 |
| 2013/0144197 | A1 * | 6/2013 | Ingimundarson | A61F 5/0123 602/16 |
| 2014/0094729 | A1 * | 4/2014 | Lachance | A61F 5/0102 602/16 |
| 2014/0142475 | A1 | 5/2014 | Goldfarb et al. | |
| 2014/0276261 | A1 * | 9/2014 | Caires | A61H 1/024 601/33 |
| 2014/0323937 | A1 * | 10/2014 | Knecht | A61F 5/0123 602/16 |
| 2015/0173929 | A1 * | 6/2015 | Kazerooni | A61F 5/0125 602/16 |
| 2015/0190262 | A1 * | 7/2015 | Capra | A61F 5/0123 602/26 |
| 2015/0351995 | A1 | 12/2015 | Zoss et al. | |
| 2016/0157562 | A1 * | 6/2016 | Yang | A44B 11/12 24/191 |
| 2016/0374887 | A1 * | 12/2016 | Wu | A61F 5/0123 623/31 |

* cited by examiner

MECHANISM FOR EFFICIENT DONNING AND DOFFING OF AN EXOSKELETON

FIELD OF THE INVENTION

The present invention pertains to the art of medical exoskeletons. More specifically, this invention describes a mechanism that allows for improved donning and doffing of a medical exoskeleton.

BACKGROUND ART

A medical exoskeleton is often divided into two sections: the exoskeleton legs (which support the user's legs), and the remaining body of the exoskeleton (which supports the user's upper body). The location at which the exoskeleton legs and remaining body of the exoskeleton connect is called the torso-leg interface. If an exoskeleton is unable to separate at the torso-leg interface, the donning and doffing processes can be quite difficult and may require assistance from another individual. However, if the exoskeleton is modular and therefore can separate at the torso-leg interface, it has been shown that the donning and doffing processes can be performed independently by the exoskeleton user with increased ease.

Examples of modular medical exoskeletons include U.S. Pat. Nos. 7,190,141 B2 and 9,101,451, B2, and U.S. Patent Application Publication No. 2015/0351995 A1. All three aforementioned examples explicitly discuss the concept of an exoskeleton that can be separated into components and configured in a plethora of embodiments (i.e., modular). However, U.S. Pat. Nos. 7,190,141 B2 and 9,101,451, B2 do not go into detail about the actual apparatus needed to connect and disconnect components of said modular exoskeleton. U.S. Application Publication No. 2015/0351995 A1 mentions that various components of a modular exoskeleton could be connected and disconnected by the user "on the fly". However, the '995 publication provides very little detail about the structure of such a connection/disconnection apparatus and only briefly mentions that a connection interface exists and is "constituted by a simple bolted connection". Thus, while the aforementioned patent documents teach a general desire for a modular exoskeleton, they do not teach infrastructure required to mechanically connect and disconnect components of a modular exoskeleton.

SUMMARY OF INVENTION

In embodiments, a manual apparatus provides for quick connection and disconnection of an exoskeleton leg from a remaining body of an exoskeleton. The manual apparatus comprises: a cavity defined by a housing coupled to the remaining body of the exoskeleton; a latch coupled to the remaining body of the exoskeleton, the latch comprising a latching feature; a clip body including a projection element extending from an end thereof, the clip body coupled to the exoskeleton leg; a handle rotatably coupled to a clip base on the clip body; and a hook rotatably coupled to the handle. When the hook is engaged with the latching feature and the handle rotated from a first unlatched position to a second latched position, the projection element moves inside the cavity.

DESCRIPTION OF EMBODIMENTS

Figure 1:
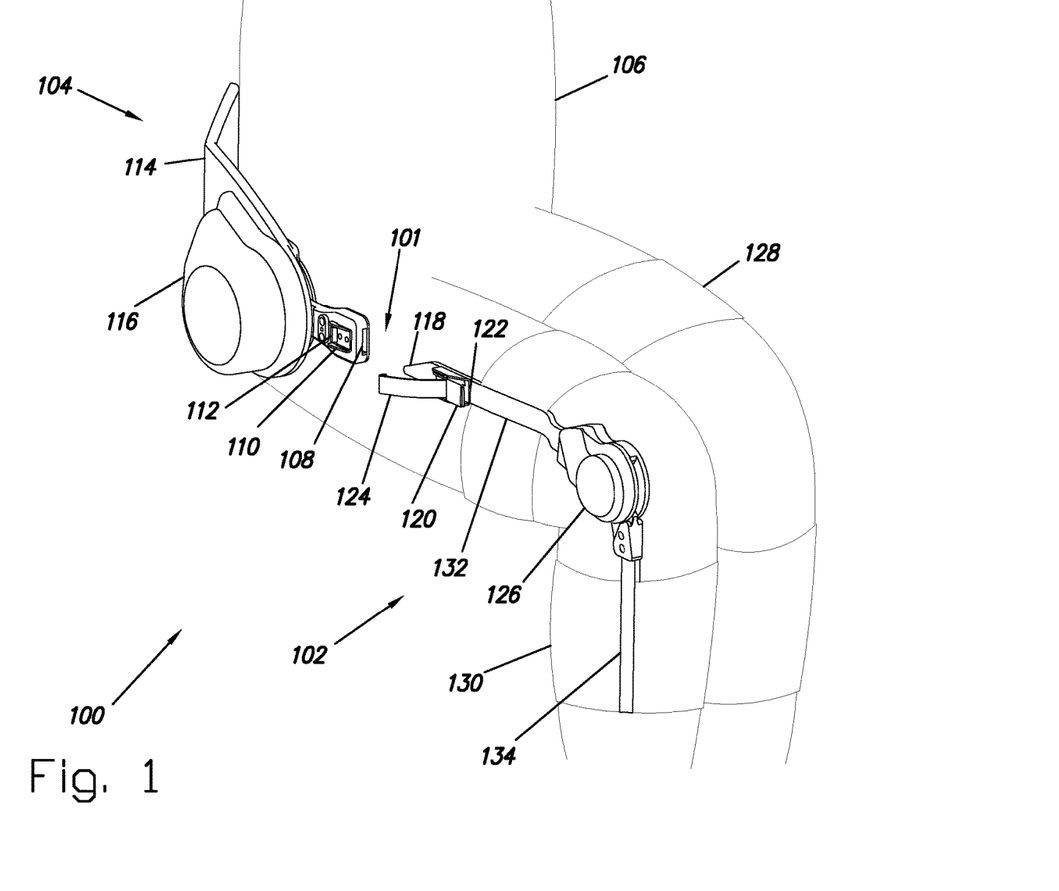
FIG. 1 is an embodiment of a medical exoskeleton in a disconnected position.

FIG. 1 shows a manual apparatus 101 for quick connection and disconnection of an exoskeleton leg 102 from the remaining body of the exoskeleton indicated at 104. Exoskeleton leg 102 and the remaining body of the exoskeleton 104 make up the entire exoskeleton 100. Typically, the entire exoskeleton 100 is worn by a user 106, as shown in FIG. 1.

Figure 2A:
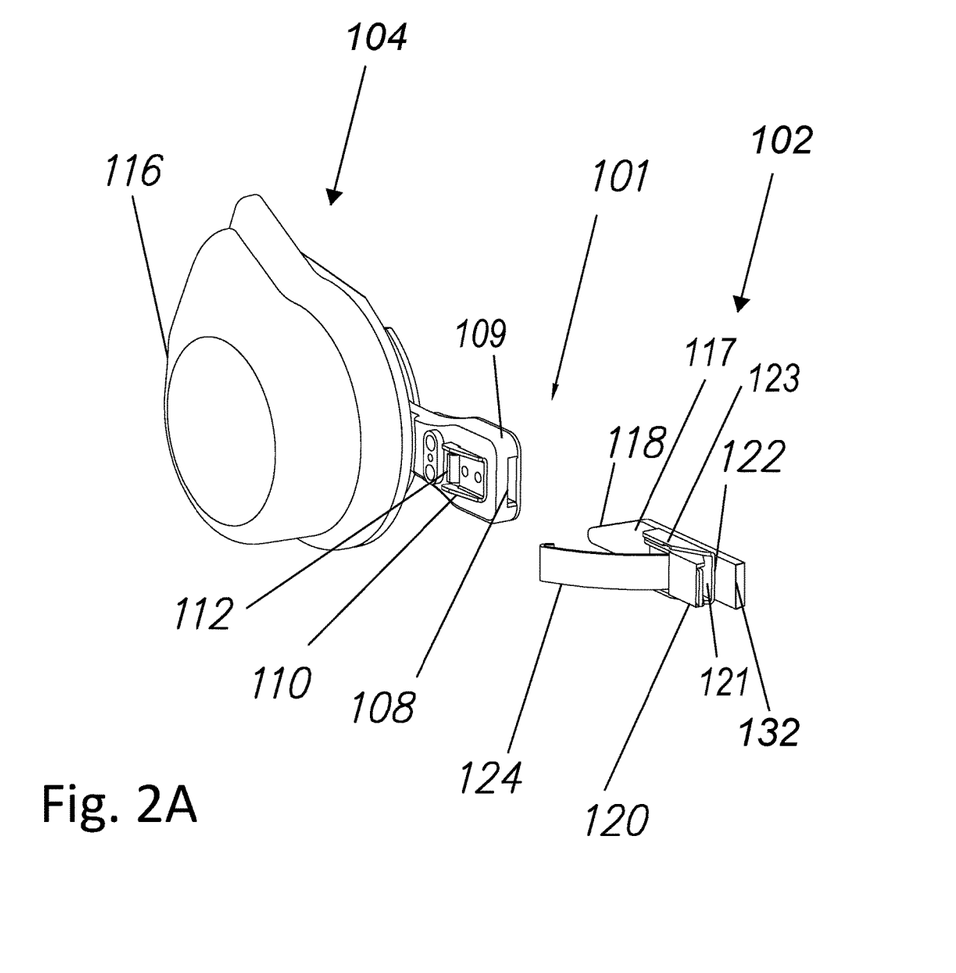
FIGS. 2A and 2B are close-up views of embodiments of a manual connection and disconnection apparatus of the present invention for a medical exoskeleton in a disconnected position.

FIG. 2A shows a close-up view of apparatus 101 as mentioned in FIG. 1. As shown in FIG. 2A, apparatus 101 comprises a cavity 108 defined by a housing 109 which is coupled to remaining body of the exoskeleton 104 as shown in FIG. 1. One of ordinary skill in the art would recognize that housing 109 can be its own independent component coupled to another element of exoskeleton 100 or manufactured as a part of another component of exoskeleton 100 that already serves a predefined function. Apparatus 101 further comprises a latch 110 formed on housing 109. In some embodiments of the invention, latch 110 comprises a latching feature (e.g., flange) 112 extending from housing 109. Similarly, an ordinary skilled in the art would recognize that latch 110 can be its own independent component coupled to another element of exoskeleton 100 or manufactured as a part of another component of exoskeleton 100 that already serves a predefined function. In addition to cavity 108 and latch 110, remaining body of the exoskeleton 104 also consists of a pelvic support 114 (shown in FIG. 1) and a hip actuator 116.

FIG. 2A also shows a clip body 117 of apparatus 101, which is coupled to exoskeleton leg 102 (shown in FIG. 1). In some embodiments of the invention, clip body 117 is formed on the exoskeleton leg 102. One of ordinary skill in the art would recognize that clip body 117 can be its own independent component coupled to another element of exoskeleton 100 or manufactured as a part of another component of exoskeleton 100 that already serves a predefined function. Clip body 117 includes a projection element 118 extending from one end thereof, and a handle 120 which is rotationally coupled to a clip base 121 mounted to clip body 117 from its first end 122. Clip body 117 additionally comprises a hook 124 which is rotationally coupled to handle 120 at a middle portion 123 of said handle 120.

FIG. 1 also shows how exoskeleton leg 102 includes a knee joint 126, thigh bracing 128, shank bracing 130, side thigh support bars 132, and shank side support bars 134. In FIG. 1, the exoskeleton leg 102 and remaining body of the exoskeleton 104 are not yet connected. Thus, FIG. 1 represents a possible orientation of user 106 during a donning process of exoskeleton 100. In this configuration, user 106 has individually donned the exoskeleton leg 102 and remaining body of the exoskeleton 104, but has yet to connect exoskeleton leg 102 and remaining body of the exoskeleton 104 together. In order to fully don exoskeleton 100, user 106 must connect exoskeleton leg 102 and remaining body of exoskeleton 104 together. This is done when hook 124 is placed onto and over latching feature 112 (i.e., when hook 124 engages latching feature 112), projection element 118 is inserted into cavity 108, and handle 120 is pushed down by user 106 to rotate handle 120 from a first unlatched position to a second latched position, thereby causing hook 124 to catch against latching feature 112, and pull clip body 117 toward housing 109 such that projection element 118 is moved into and retained within cavity 108.

Figure 2B:
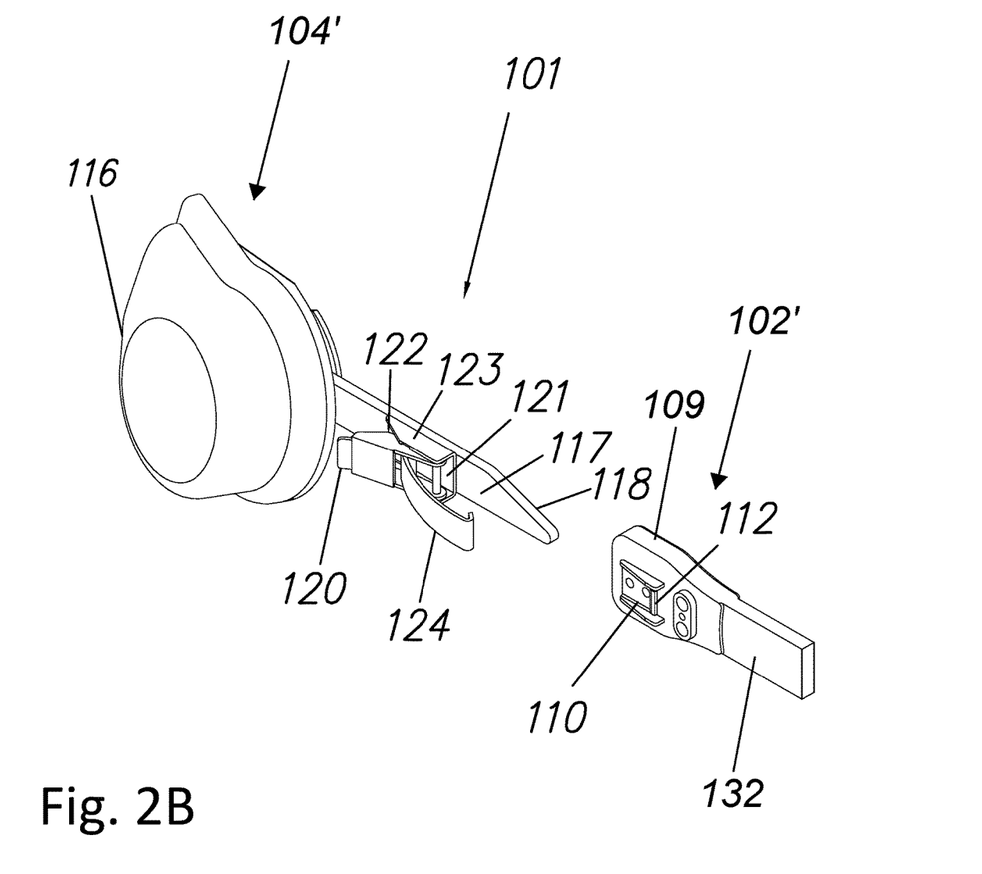

With reference to FIG. 2B, an alternative embodiment is shown wherein a clip body 117 is coupled to a remaining body of the exoskeleton 104', and the latching feature 112 is coupled to an exoskeleton leg 102'. The cavity 108 is defined by the housing 109' coupled to a first component of the exoskeleton (102'), and the latch 110 is coupled to the first component of the exoskeleton (102'), wherein the latch 110 comprises the latching feature 112. Further, the clip body 117 includes the projection element 118 extending therefrom; the clip body 117 is coupled to a second component of the exoskeleton (104'); the handle 120 is rotatably coupled to the clip base 121 on the clip body 117; and the hook 124 is rotatably coupled to the handle 120, wherein when the hook 124 is engaged with the latching feature 112 and when the handle 120 is rotated from a first unlatched position to a second latched position, said projection element 118 moves inside the cavity 108.

Figure 3:
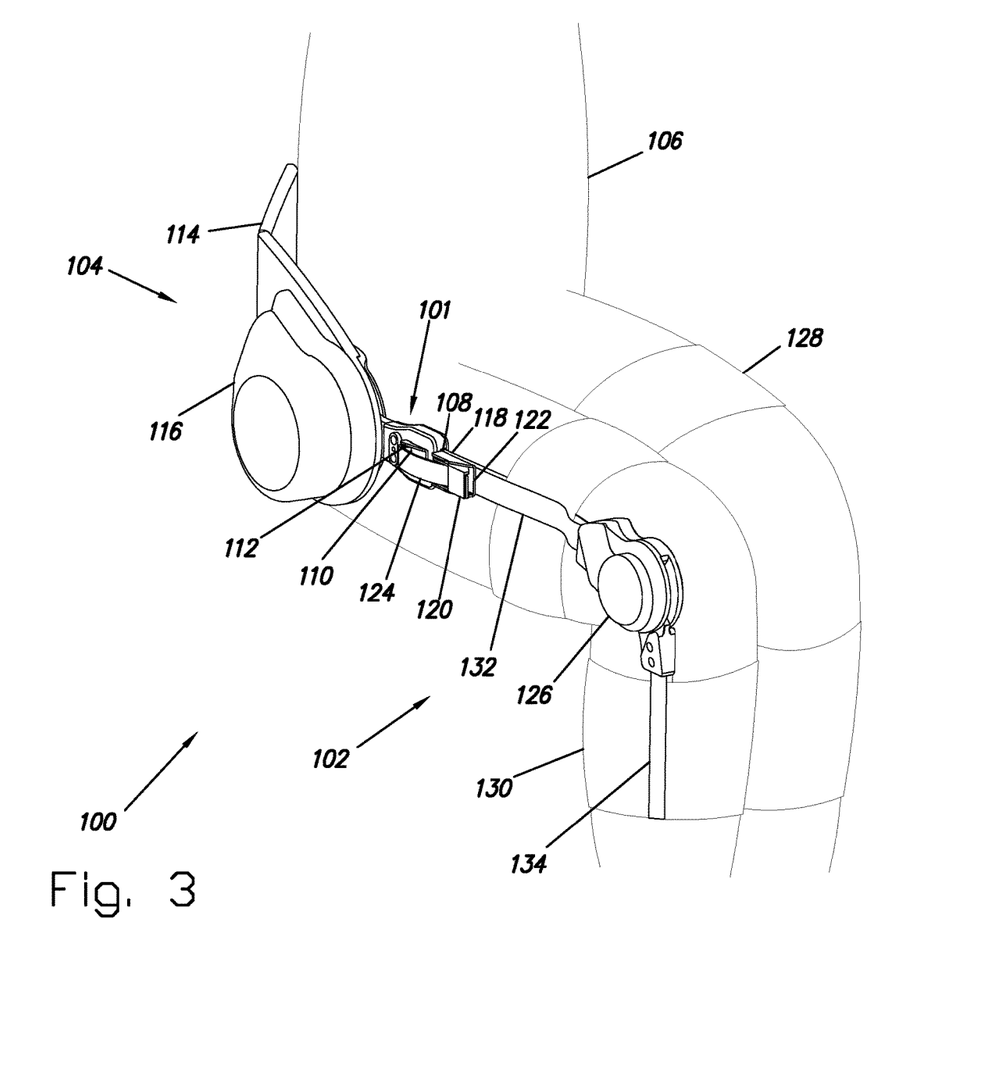
FIG. 3 is an embodiment of a medical exoskeleton in a connected position.

FIG. 3 shows an embodiment of exoskeleton 100 where exoskeleton leg 102 and remaining body of the exoskeleton 104 are connected together. In FIG. 3, projection element 118 is firmly inside of cavity 108. In this configuration, user 106 has completed the donning process and would be able to stand up and walk. Manual apparatus 101 is what allows for projection element 118 and cavity 108 to connect. Although FIG. 3 shows the embodiment of FIG. 2A connected, it should be understood that the components of the embodiment of FIG. 2B connect in the same manner.

Figure 4:
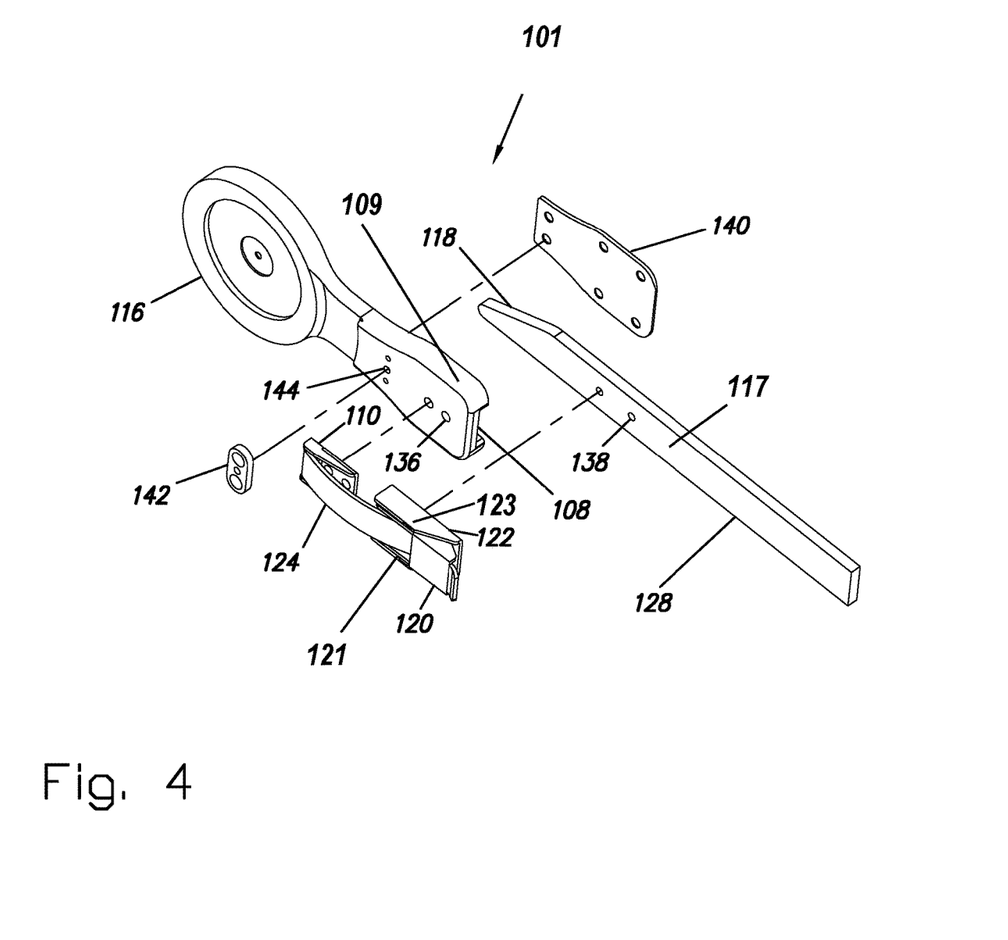
FIG. 4 is an exploded view of a manual connection and disconnection apparatus for a medical exoskeleton.

FIG. 4 shows an exploded view of a manual apparatus 101. Manual apparatus 101 includes a housing 109 defining a cavity 108, which is an extension of the hip actuator 116 on remaining body of the exoskeleton 104 (shown in FIG. 1). Additionally, manual apparatus 101 includes a clip body 117 in the form of thigh bracing 128 on exoskeleton leg 102. Clip body 117 includes a projection element 118 extending from one end thereof, which is an extension of thigh bracing 128. Manual apparatus 101 works by providing user 106 with a significant mechanical advantage during connection and separation of exoskeleton leg 102 and remaining body of the exoskeleton 104.

As shown in FIG. 4, manual apparatus 101 is a three-bar mechanism that comprises a handle 120 which is rotatably coupled to a clip base 121, adapted to be mounted to clip body 117 from its first end 122. Apparatus 101 additionally comprises a hook 124 (third link) which is rotatably coupled to handle 120 at a middle portion 123 of said handle 120. Apparatus 101 further comprises a latch 110 which is coupled to remaining body of the exoskeleton 104. Latch 110 includes a latching feature 112 (shown in FIG. 5). When user 106 is attempting to draw projection element 118 into cavity 108, he or she can make use of manual apparatus 101 to assist in drawing projection element 118 into cavity 108 with ease. To make manual apparatus 101 effective, latch 110 is fixed to housing 109 on remaining body of exoskeleton 104 via fasteners (not shown) extending through holes 136 in housing 109. Additionally, first end 122 is fixed to clip body 117 on exoskeleton leg 102 via fasteners (not shown) extending through holes 138 in clip body 117. Once user 106 places hook 124 onto latching feature 112 of latch 110, manual apparatus 101 can be used to easily draw projection element 118 into cavity 108 by applying an appropriate force to handle 120. Once this is done, the over-center design of manual apparatus 101 is able to constrain projection element 118 and cavity 108 such that no relative motion occurs and projection element 118 remains inside cavity 108.

FIG. 4 also shows how a cover plate 140 is fixed to remaining body of exoskeleton 104 and encloses the medial side of cavity 108. Cover plate 140 restricts the manual apparatus 101 to one degree of freedom (projection element 118 sliding in and out of cavity 108). Without cover plate 140, projection element 118 could easily fall out of cavity 108. Cover plate 140 is fixed to remaining body of exoskeleton 104 via fasteners (not shown). Finally, a stopper 142 is fixed to holes 144 on remaining body of exoskeleton 104. Stopper 142 acts as a hard stop for hook 124 to press against when separating projection element 118 from cavity 108. The purpose of stopper 142 is explained in more clarity in FIG. 5.

Figure 5:
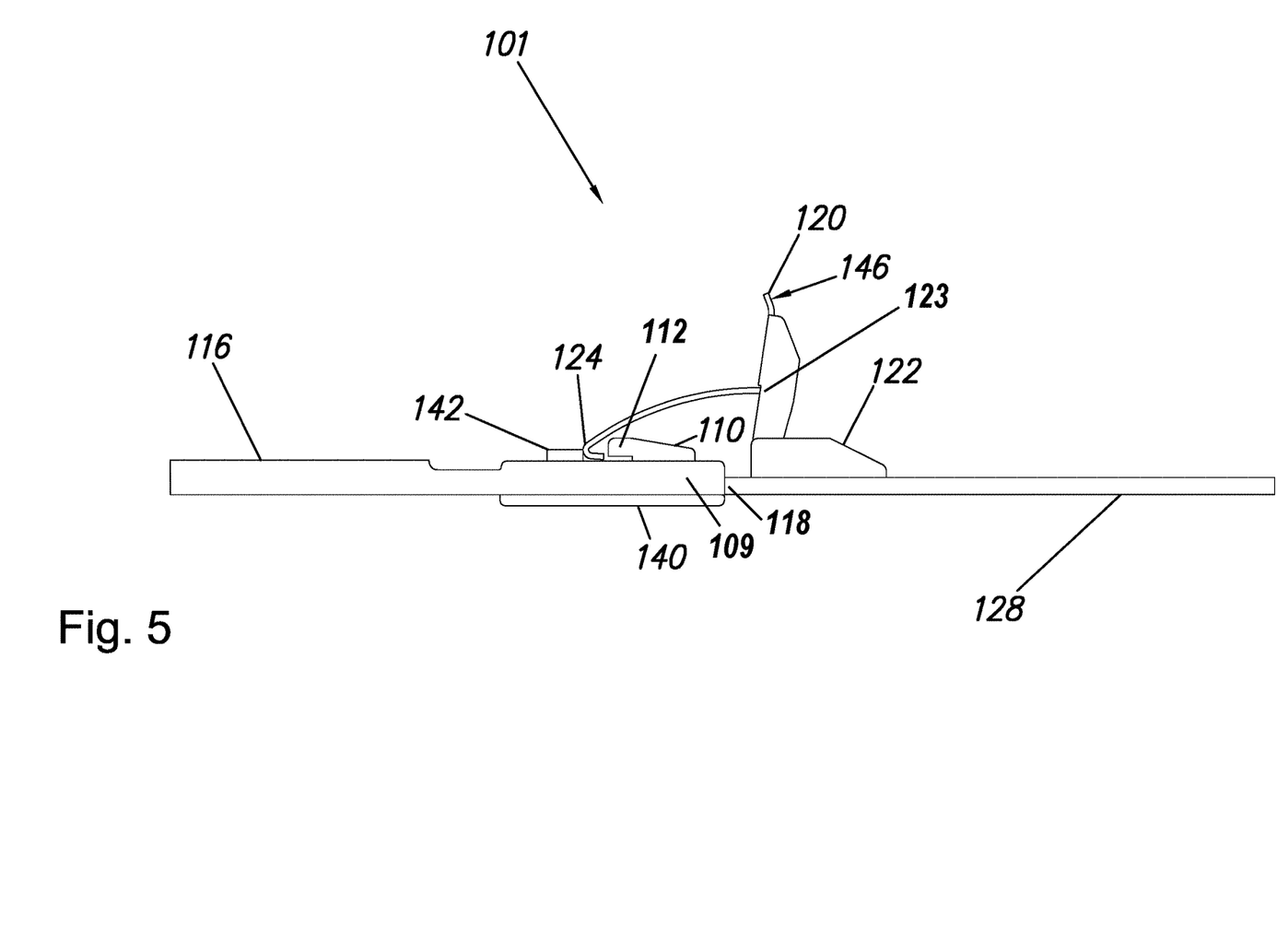
FIG. 5 is an isolated view of a manual connection and disconnection apparatus for a medical exoskeleton during doffing.

FIG. 5 shows only manual apparatus 101 and excludes the other components that comprise exoskeleton 100. FIG. 5 is provided to better show the purpose of stopper 142 during the doffing process of exoskeleton 100. During doffing, user 106 attempts to separate remaining body of the exoskeleton 104 from exoskeleton leg 102 by removing projection element 118 from cavity 108. Although manual apparatus 101 provides a significant mechanical advantage to assist the donning process, without stopper 142, manual apparatus 101 provides no mechanical advantage during the doffing process. FIG. 5 mimics a situation where user 106 is attempting to doff exoskeleton 100. It is shown that hook 124 of manual apparatus 101 has separated from latch 110 of manual apparatus 101. Now, hook 124 of manual apparatus 101 is pressing against stopper 142. Because stopper 142 is fixed to remaining body of the exoskeleton 104, stopper 142 acts as a hard stop for hook 124 during the doffing process. Thus, by applying a force in the direction of arrow 146 at handle 120, user 102 is able to experience a mechanical advantage while separating projection element 118 (male piece) and housing 109 (female piece). This mechanical advantage is an important characteristic, as oftentimes friction makes it difficult to separate male piece 118 and female piece 109. Without stopper 142 acting as a hard stop for latch 124, this mechanical advantage during doffing would not be possible.

Figure 6:
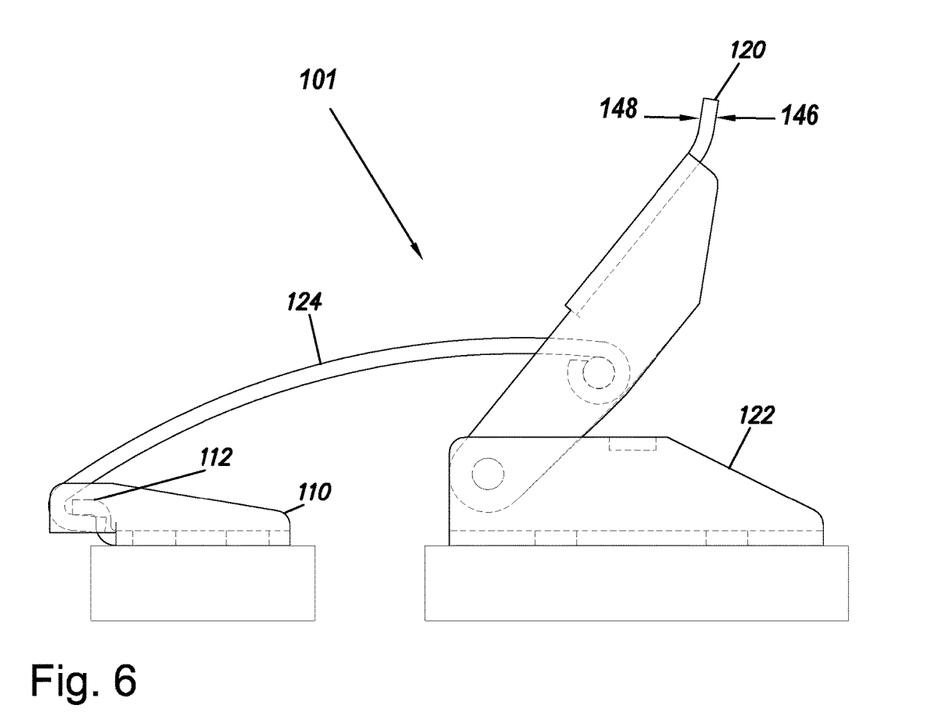
FIG. 6 is a side profile of the handle, hook, latch, and base of a manual connection and disconnection apparatus for a medical exoskeleton.
Figure 7:
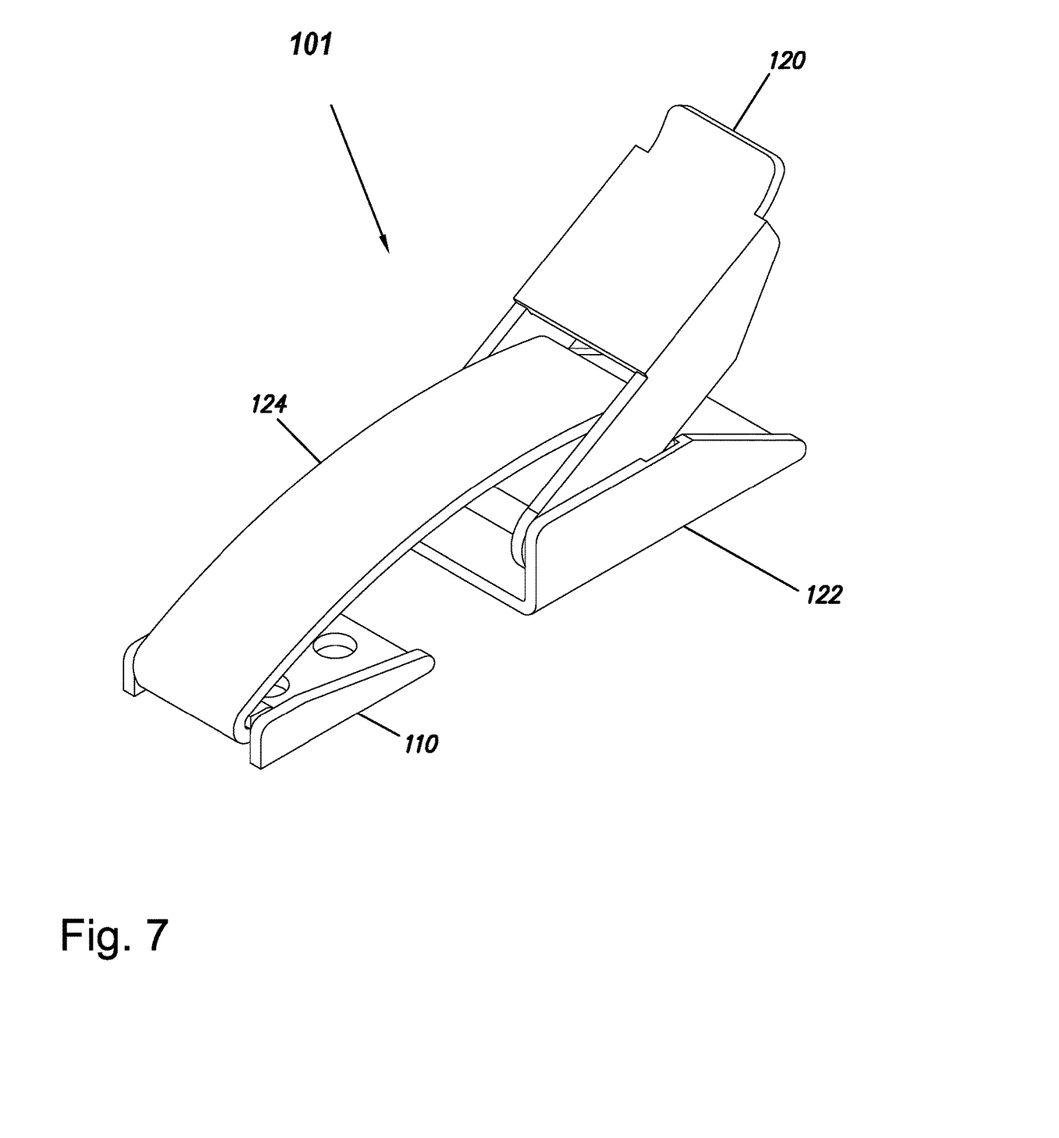
FIG. 7 is an isometric view of the handle, hook, latch, and base shown in FIG. 5, shown in a connected position.
Figure 8:
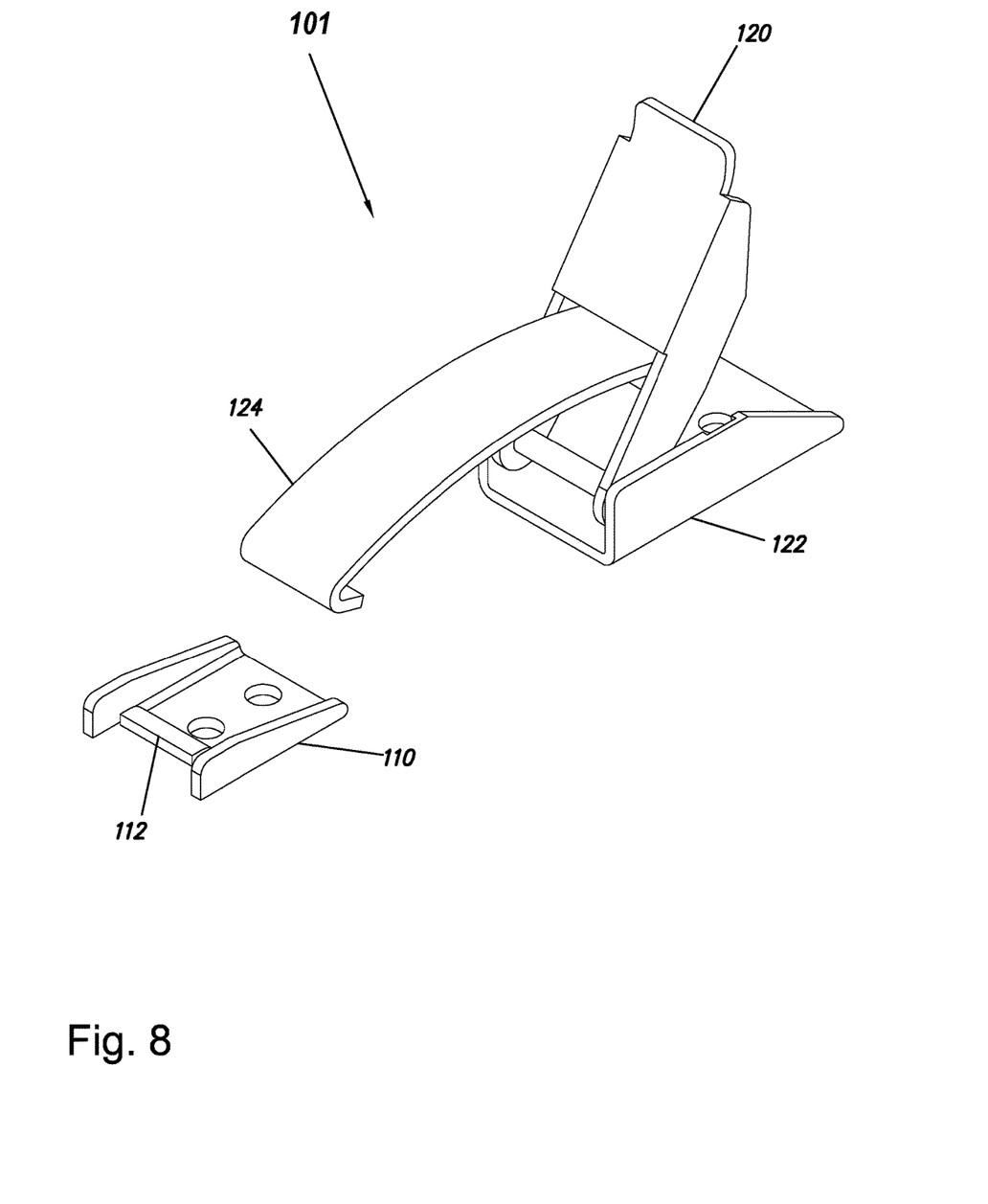
FIG. 8 is an isometric view of the handle, hook, latch and base shown in FIG. 5, shown in a disconnected position.

For clarity, FIGS. 6, 7, and 8 show different views of manual apparatus 101. FIG. 7 and FIG. 8 are isometric views of manual apparatus 101 in connected and disconnected configurations, respectively. FIG. 6 shows a side view of manual apparatus 101 and also depicts arrows 146 and 148. These arrows are designed to show the directions in which forces can be applied to handle 120 of manual apparatus 101. If a sufficient force is applied in the direction of arrow 148, manual apparatus 101 will pull projection element 118 of exoskeleton leg 102 into cavity 108 of remaining body of exoskeleton 104. Thus, a force in the direction of arrow 148 would be useful during the donning of exoskeleton 100. If a sufficient force is applied in the direction of arrow 146, manual apparatus 101 will pull projection element 118 of exoskeleton leg 102 out of cavity 108 of remaining body of exoskeleton 104 (using stopper 142 as described previously). Thus, a force in the direction of arrow 146 would be useful during doffing. In summary, user 106 pushes handle 120 towards themselves (i.e., towards an outer surface of their leg) along the direction of arrow 148 for insertion of projection element 118 into cavity 108. Further, user 106 pushes handle 120 away from themselves (i.e., away from an outer surface of their leg) in the direction of arrow 146 for removal of projection element 118 from cavity 108.

Figure 9:
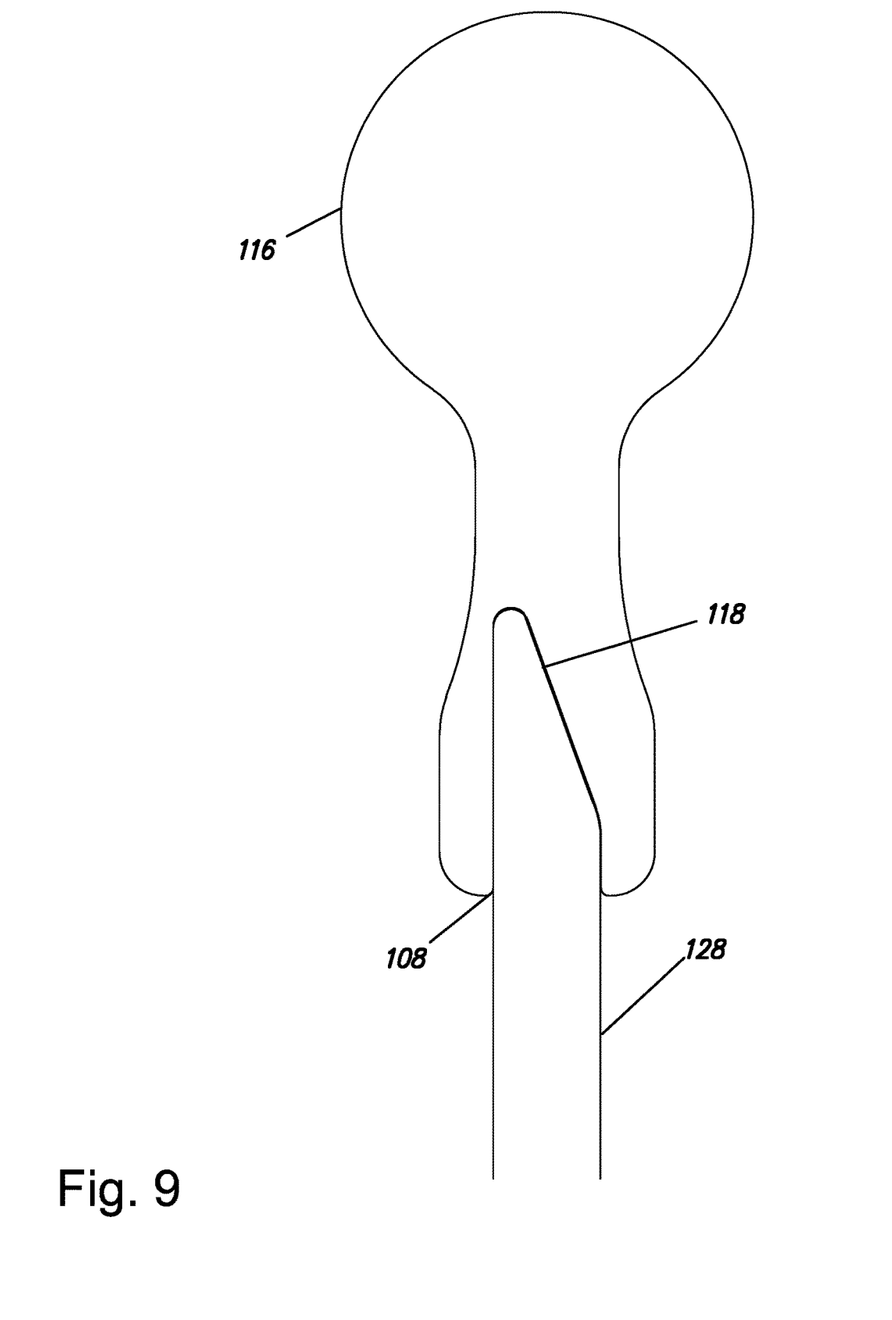
FIG. 9 is a side profile of a mating interface of a manual connection and disconnection apparatus for a medical exoskeleton, shown in the connected position.
Figure 10:
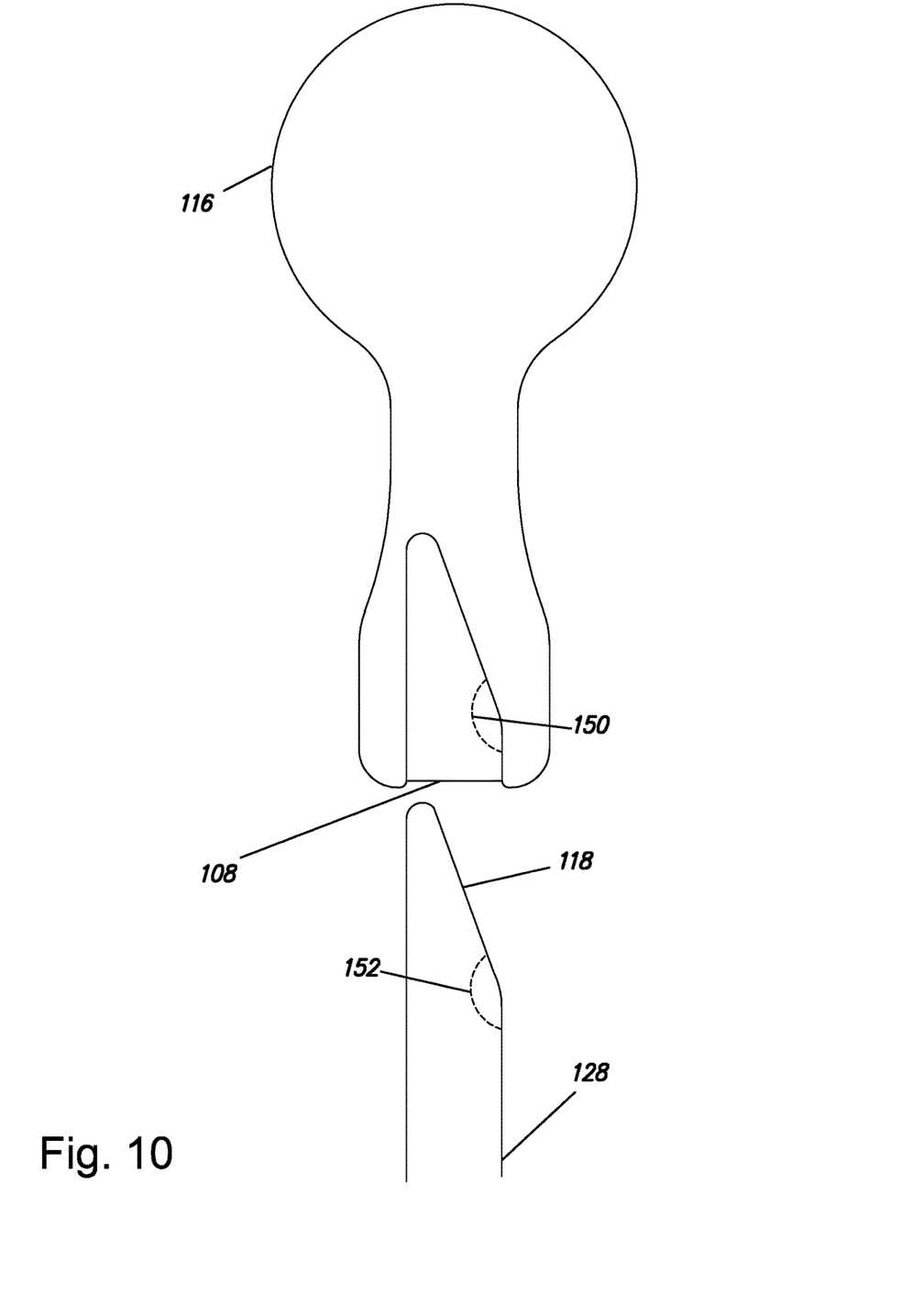
FIG. 10 is a side profile of the mating interface shown in FIG. 9, shown in a disconnected position.

FIG. 9 and FIG. 10 show side views of the mating interface of projection element 118 and cavity 108. FIG. 9 shows the connected position, when projection element 118 is fully inserted inside of cavity 108. FIG. 10 shows the disconnected position, when projection element 118 is completely outside of cavity 108. In this embodiment, the mating interface of manual apparatus 101 makes use of a wedging contour. The purpose of this design is to ensure that no relative motion occurs between projection element 118 and cavity 108 when projection element 118 is fully inserted into cavity 108. Relative movement between projection element 118 and cavity 108 would result in an inefficient transfer of torque between hip actuator 116 and exoskeleton leg 102 during walking. By making an angle 150 (the contour angle of cavity 108) and an angle 152 (the contour angle of projection element 118) equivalent, significant area contact occurs between projection element 118 and cavity 108 during walking. This area contact helps distribute the pressures from varying loads, which helps prevent localized yielding. If angle 150 and angle 152 were not equivalent, loading pressures would not be as distributed, which could cause localized yielding during walking.

What is claimed is:

1. A manual apparatus for quick connection and disconnection of components of an exoskeleton, said manual apparatus comprising:
   a clip body, comprising a projection element extending from an end thereof, said clip body configured to be coupled to an exoskeleton leg of said exoskeleton;
   a cavity, defined by a housing on a remaining body of said exoskeleton;
   a latch, coupled to said remaining body of said exoskeleton, said latch comprising a latching feature;
   a handle, rotatably coupled to a clip base on said clip body;
   a hook, rotatably coupled to said handle; wherein when said hook is engaged with said latching feature and said handle is rotated from a first unlatched position to a second latched position, said projection element is drawn into said cavity, thereby connecting said exoskeleton leg to said remaining body of said exoskeleton; and
   a stopper disposed on said housing, wherein when said handle is rotated from said second latched position to said first unlatched position while said stopper constrains said hook, said projection element is drawn out of said cavity, thereby disconnecting said exoskeleton leg from said remaining body of said exoskeleton.

2. The manual apparatus of claim 1, wherein the manual apparatus is configured to enable one-handed attachment of said exoskeleton leg to said remaining body of said exoskeleton.

3. The manual apparatus of claim 1, wherein when said handle is rotated from said second latched position to said first unlatched position, said projection element is drawn out of said cavity thereby disconnecting said exoskeleton leg from said remaining body of said exoskeleton.

4. The manual apparatus of claim 1, wherein said projection element is an integral part of said exoskeleton leg.

5. The manual apparatus of claim 1, wherein said housing is an integral part of said remaining body of said exoskeleton.

6. The manual apparatus of claim 1, wherein said latch is an integral part of said remaining body of said exoskeleton.

7. The manual apparatus of claim 1, wherein said cavity is formed with a contour angle that matches a contour angle of said projection element, such that no relative motion occurs between said projection element and said cavity when said projection element is fully inserted into said cavity.

8. A manual apparatus for quick connection and disconnection of components of an exoskeleton, said manual apparatus comprising:
   a clip body, comprising a projection element extending therefrom, said clip body configured to be coupled to a first component of said exoskeleton;
   a cavity, defined by a housing coupled to a second component of said exoskeleton,
   wherein said second component of said exoskeleton is separate and distinct from said first component of said exoskeleton when in a disconnected position;
   a latch, coupled to either said first or said second component of said exoskeleton,
   said latch comprising a latching feature;
   a handle, rotatably coupled to a component of said exoskeleton opposite said latch;
   a hook, rotatably coupled to said handle, wherein when said hook is engaged with said latching feature and said handle is moved from a first unlatched position to a second latched position, said projection element moves is drawn into inside said cavity, thereby connecting said first component of said exoskeleton to said second component of said exoskeleton; and
   a stopper disposed on said housing, wherein when said handle is rotated from said second latched position to said first unlatched position while said stopper constrains said hook, said projection element is drawn out of said cavity, thereby disconnecting first component of said exoskeleton from said second component of said exoskeleton.

9. The manual apparatus of claim 8, wherein said first component is an exoskeleton leg and said second component is a remaining body of said exoskeleton.

10. The manual apparatus of claim 8, wherein said second component is an exoskeleton leg and said first component is a remaining body of said exoskeleton.

11. The manual apparatus of claim 8, wherein said projection element is an integral part of said first component.

12. The manual apparatus of claim 8, wherein said housing is an integral part of said second component.

13. The manual apparatus of claim 8, wherein said latch is an integral part of said second component.

14. The manual apparatus of claim 8, wherein said latch is a part of said second component.

15. The manual apparatus of claim 8, further comprising a stopper feature wherein when said handle is rotated from said second latched position to said first unlatched position while said stopper feature constrains said hook, said projection element is drawn out of said cavity, thereby disconnecting said first component from said second component.

16. The manual apparatus of claim 8, wherein said cavity is formed with a contour angle that matches a contour angle of said projection element, such that no relative motion occurs between said projection element and said cavity when said projection element is fully inserted into said cavity.

17. A manual apparatus for quick connection and disconnection of components of an exoskeleton, said manual apparatus comprising:
   a cavity, defined by a housing configured to be coupled to an exoskeleton leg of an exoskeleton;
   a latch, coupled to said housing, said latch comprising a latching feature;
   a clip body, comprising a projection element extending therefrom, said clip body configured to be coupled to a remaining body of said exoskeleton;
   a handle, rotatably coupled to said clip body;
   a hook, rotatably coupled to said handle, wherein when said hook is engaged with said latching feature and said handle is moved from a first unlatched position to a second latched position, said projection element is drawn into said cavity, thereby connecting said exoskeleton leg to said remaining body of said exoskeleton; and
   a stopper on said housing, wherein when said handle is rotated from said second latched position to said first unlatched position while said stopper constrains said hook, said projection element is drawn out of said cavity, thereby disconnecting said exoskeleton leg from said remaining body of said exoskeleton.

18. The manual apparatus of claim 17, wherein said projection element is adapted to be received within an opening formed in a side wall of said housing, and said latch extends from a top wall of Currently Amended housing.

19. The manual apparatus of claim 17, wherein said projection element is an integral part of said remaining body of said exoskeleton.

20. The manual apparatus of claim 17, wherein said cavity is an integral part of said exoskeleton leg.

21. The manual apparatus of claim 17, wherein said cavity is formed with a contour angle that matches a contour angle of said projection element, such that no relative motion occurs between said projection element and said cavity when said projection element is fully inserted into said cavity.

22. A manual apparatus for quick connection and disconnection of components of an exoskeleton, said manual apparatus comprising:
   a clip body, comprising a clip base and a projection element extending from an end thereof,
   the clip body configured to be coupled to an exoskeleton leg of said exoskeleton;
   a cavity, defined by a housing on an exoskeleton torso of said exoskeleton;
   a latch, coupled to said exoskeleton torso, said latch comprising a latching feature;
   a handle, rotatably coupled to said clip base on said clip body;
   a hook, rotatably coupled to said handle;
   wherein when said hook is engaged with said latch and said handle is rotated from a first unlatched position to a second latched position, said projection element of said clip body is drawn into said cavity, thereby connecting said exoskeleton leg to said exoskeleton torso; and
   a stopper on said housing, wherein when said handle is rotated from said second latched position to said first unlatched position while said stopper constrains said hook, said projection element is drawn out of said cavity, thereby disconnecting said exoskeleton leg from said exoskeleton torso.

23. The manual apparatus of claim 22, wherein said cavity is formed with a contour angle that matches a contour angle of said projection element, such that no relative motion occurs between said projection element and said cavity when said projection element is fully inserted into said cavity.

* * * * *